(12) United States Patent
Meyer et al.

(10) Patent No.: US 9,839,431 B2
(45) Date of Patent: Dec. 12, 2017

(54) OCCLUSION DEVICES AND METHODS OF MAKING AND USING SAME

(71) Applicant: AGA Medical Corporation, Plymouth, MN (US)

(72) Inventors: Michael Meyer, Minnetrista, MN (US); Benedict Skemp, Golden Valley, MN (US); Tracee Eidenschink, Wayzata, MN (US); Edward E. Parsonage, St. Paul, MN (US)

(73) Assignee: ST. JUDE MEDICAL, CARDIOLOGY DIVISION INC., St. Paul, MN (US)

(*) Notice: Subject to any disclaimer, the term of this patent is extended or adjusted under 35 U.S.C. 154(b) by 277 days.

(21) Appl. No.: 14/595,686

(22) Filed: Jan. 13, 2015

(65) Prior Publication Data

US 2015/0196305 A1    Jul. 16, 2015

Related U.S. Application Data

(60) Provisional application No. 61/927,176, filed on Jan. 14, 2014.

(51) Int. Cl.
*A61B 17/12* (2006.01)
*A61B 17/00* (2006.01)

(52) U.S. Cl.
CPC .. *A61B 17/12181* (2013.01); *A61B 17/12031* (2013.01); *A61B 17/12122* (2013.01); *A61B 17/12136* (2013.01); *A61B 17/12168* (2013.01); *A61B 17/12177* (2013.01); *A61B 17/12195* (2013.01); *A61B 2017/00871* (2013.01); *A61B 2017/12054* (2013.01); *A61B 2017/12095* (2013.01)

(58) Field of Classification Search
CPC ........ A61B 17/12181; A61B 17/12031; A61B 17/12122; A61B 17/12168; A61B 17/12136; A61B 17/12195
USPC ......... 606/151, 153, 192, 194, 200, 213, 63; 623/1.11, 1.18, 1.42, 1.44, 9
See application file for complete search history.

(56) References Cited

U.S. PATENT DOCUMENTS

| | | | | |
|---|---|---|---|---|
| 8,449,592 | B2 * | 5/2013 | Wilson | A61B 17/12022 623/1.11 |
| 9,051,411 | B2 * | 6/2015 | Wilson | B82Y 30/00 |
| 2005/0165480 | A1 * | 7/2005 | Jordan | A61B 17/12022 623/9 |
| 2005/0234540 | A1 * | 10/2005 | Peavey | A61B 17/12022 623/1.18 |
| 2013/0165966 | A1 * | 6/2013 | Widomski | A61B 17/0057 606/213 |
| 2013/0237908 | A1 | 9/2013 | Clark | |

* cited by examiner

*Primary Examiner* — Vy Bui
(74) *Attorney, Agent, or Firm* — Armstrong Teasdale LLP (57) ABSTRACT

The present disclosure provides improved medical devices for occluding a left atrial appendage. In one embodiment, the medical device includes a temperature activated memory shape foam that is constructed to transition from a first collapsed conformation to a second expanded conformation upon an increase in temperature such that it can expand to provide an occlusive benefit inside a left atrial appendage. In another embodiment the medical device includes a flowable thermoset that is injected into the left atrial appendage where is it cured so that it may assume the conformation of the left atrial appendage and provide an occlusive benefit.

9 Claims, 8 Drawing Sheets

OCCLUSION DEVICES AND METHODS OF MAKING AND USING SAME

CROSS-REFERENCE TO RELATED APPLICATIONS

This application claims priority from U.S. Provisional Patent Application Ser. No. 61/927,176, filed on Jan. 14, 2014, which is herein incorporated by reference in its entirety.

BACKGROUND OF THE DISCLOSURE a. Field of the Disclosure

The present disclosure generally relates to medical devices and methods for occluding a body lumen, cavity, or hole. In particular, the present disclosure relates to occlusion devices, and related methods, for achieving improved left atrial appendage occlusion.

b. Background Art

A variety of medical devices are used in medical procedures. Certain intravascular devices, such as delivery catheters and guidewires, are generally used to deliver fluids or other medical devices to specific locations within a patient's body, such as a selective site within the circulation system. Other frequently more complex devices are used in treating specific conditions, such as devices used in removing vascular occlusions or for treating septal defects and the like.

In many circumstances, it may be desirable or necessary to occlude a patient's vessel, chamber, channel, hole, cavity, or the like so as to stop blood flow therethrough. For example, atrial fibrillation may result in the formation of one or more blood clots in the left atrial appendage, which is a tapered, pouch-like extension located in the upper left chamber of the heart. A blood clot that breaks loose from the left atrial appendage may migrate through the blood vessels and eventually occlude a smaller vessel in the brain or heart resulting in a stroke or heart attack. By occluding the left atrial appendage, the formation and release of blood clots from this area may be significantly reduced or eliminated altogether.

Various techniques have been developed to occlude the left atrial appendage. Such techniques may include medication, surgery, or minimally invasive techniques. Other closure methods include epicardial left atrial appendage ligation and surgical closure.

SUMMARY OF THE DISCLOSURE

The present disclosure is directed to a medical device for occluding a left atrial appendage. The medical device comprises a foam structure having a distal end and a proximal end, the foam structure being constructed to transition from a first conformation to a second conformation upon an increase in temperature. The second conformation is configured to occlude the left atrial appendage.

The present disclosure is further directed to a medical device for occluding a left atrial appendage. The medical device comprises a flowable thermoset and a distribution member having a proximal end and a distal end and including means for allowing the flowable thermoset to pass therethough and into the left atrial appendage.

The present disclosure is further directed to a method of occluding a left atrial appendage, the method comprising: introducing a medical device having a proximal end and a distal end into the interior of the left atrial appendage, the medical device having a means for allowing a flowable thermoset to pass therethough and into the left atrial appendage; introducing a flowable thermoset through the medical device and into the left atrial appendage; and allowing the flowable thermoset to set and occlude the left atrial appendage.

The present disclosure is further directed to a method of occluding a left atrial appendage, the method comprising: introducing a medical device comprising a foam structure in a first conformation into the left atrial appendage and allowing the foam structure to transition into a second conformation, wherein the second conformation occludes the left atrial appendage.

DETAILED DESCRIPTION OF THE DISCLOSURE

It is desirable to be able to provide a medical device that can occlude the left atrial appendage of a human heart so as to prevent the escape of blood clots therefrom, irrespective of the exact size and shape of the left atrial appendage, which can vary greatly from one individual to another. It is also desirable to provide methods of forming and using such a medical device. The present disclosure is directed to medical devices for occluding the left atrial appendage, and methods of forming and using the medical devices, that are well suited for use in a variety of individuals irrespective of the specific size and shape of the left atrial appendage of the individual.

The medical devices described herein are designed for delivery to the left atrial appendage of the human heart through a delivery catheter, sheath, or the like. In one embodiment, the medical device includes a temperature activated memory shape foam that is constructed to transition from a first collapsed conformation to a second expanded conformation upon an increase in temperature (i.e., the transition temperature of the material). The second expanded conformation is pliable and configured to substantially mold itself to the anatomy of a left atrial appendage to provide an occlusive benefit, and may be recaptured/repositioned/removed if desired. In another embodiment, the medical device includes a flowable thermoset and a flow member including means for allowing a flowable thermoset to pass therethough and into the left atrial appendage. Once inside of the left atrial appendage, the flowable thermoset shapes and conforms itself and cures/solidifies to occlude the left atrial appendage.

When a medical device of the present disclosure is introduced into the left atrial appendage, it ultimately substantially conforms to the size and shape of the left atrial appendage to form a custom polymer plug-like occlusion device that can occlude the left atrial appendage and substantially reduce or eliminate the formation and migration of blood clots therefrom and into the body. These medical devices result in improved patient safety and reduce or eliminate the need for multiple sizes and shapes of occlusion devices for the left atrial appendage.

In some embodiments of the present disclosure, the medical device for occluding the left atrial appendage is formed into a first conformation as described herein and may be inserted into a delivery catheter, or other delivery device, in a collapsed or condensed configuration; that is, a configuration that is smaller than the final configuration that will provide an occlusive benefit within the left atrial appendage. The medical device is then advanced through the delivery catheter and out a distal end of the delivery catheter at a desired treatment site, such as at the left atrial appendage. At this time, due to an increase in temperature present in the body (or other temperature activation means such as a warm saline injection), the temperature of the device will rise above a set transition temperature of the device and it will expand into a second expanded conformation to occlude the left atrial appendage as described herein.

In other embodiments, the medical device for occluding the left atrial appendage is in the form of a liquid or gel, or combination of liquids and/or gels, and is injected into the left atrial appendage through a delivery catheter, delivery lumen, or the like, and allowed to set or cure inside of the left atrial appendage. Upon setting or curing, the medical device conforms to the shape and size of the left atrial appendage thus providing an occlusive benefit.

In many embodiments, the medical devices described herein are designed to be compatible with multiple commercially available delivery systems. Additionally, in many embodiments the medical devices are designed to be acutely recapturable so that in the event it is desired to remove and/or reposition the device after placement, it can be easily recaptured and removed or repositioned.

It has been unexpectedly found that the medical devices described herein and formed in the left atrial appendage are highly compliant to the anatomy and can conform to a left atrial appendage and create a seal therein to prevent the formation and escape of blood clots from the left atrial appendage. The medical devices provide an improved occlusive benefit irrespective of the exact size and shape of the left atrial appendage due to their highly compliant nature. Because the medical devices described herein are capable of conforming to different sized and shaped left atrial appendages without a loss of occlusive benefit, they are advantageous as they reduce or eliminate the need to have multiple sized and shaped occlusive medical devices for practitioners to choose from prior to or during a procedure, and substantially reduce or eliminate the need to recapture/reposition/remove a left atrial appendage occlusive device due to improper sizing and/or fit.

In one embodiment of the present disclosure, there is provided a medical device for occluding a left atrial appendage that includes a temperature activated memory shape foam (foam structure) that has a distal end and a proximal end. The temperature activated memory shape foam is constructed such that it assumes a first conformation that is compacted, condensed, or collapsed such that it has a higher density as compared to the density of the temperature activated memory shape foam in a second expanded conformation. The medical device is in the first conformation when it is delivered into the left atrial appendage through a delivery catheter or other delivery device as known in the art. In some embodiments, the temperature activated memory shape foam may be constrained by an outer sheath as is known in the art that may be pulled back to expose the medical device once it is properly positioned inside of the left atrial appendage. The temperature activated memory shape foam is constructed such that it transforms and assumes a second expanded conformation upon reaching a desired activation temperature; that is, an increased temperature within the human body. This second expanded conformation is assumed after the medical device in introduced into the left atrial appendage. Once expanded within the left atrial appendage, it is this second expanded conformation that provides the occlusive benefit within the left atrial appendage. The expanded conformation may be achieved after delivery into the left atrial appendage in a time period from about 10 seconds to about 2 minutes, including from about 10 seconds to about 1 minute, including from about 10 seconds to about 20 seconds. In some embodiments, the expanded conformation may be achieved in from about 30 seconds to about 1 minute.

Figure 1:
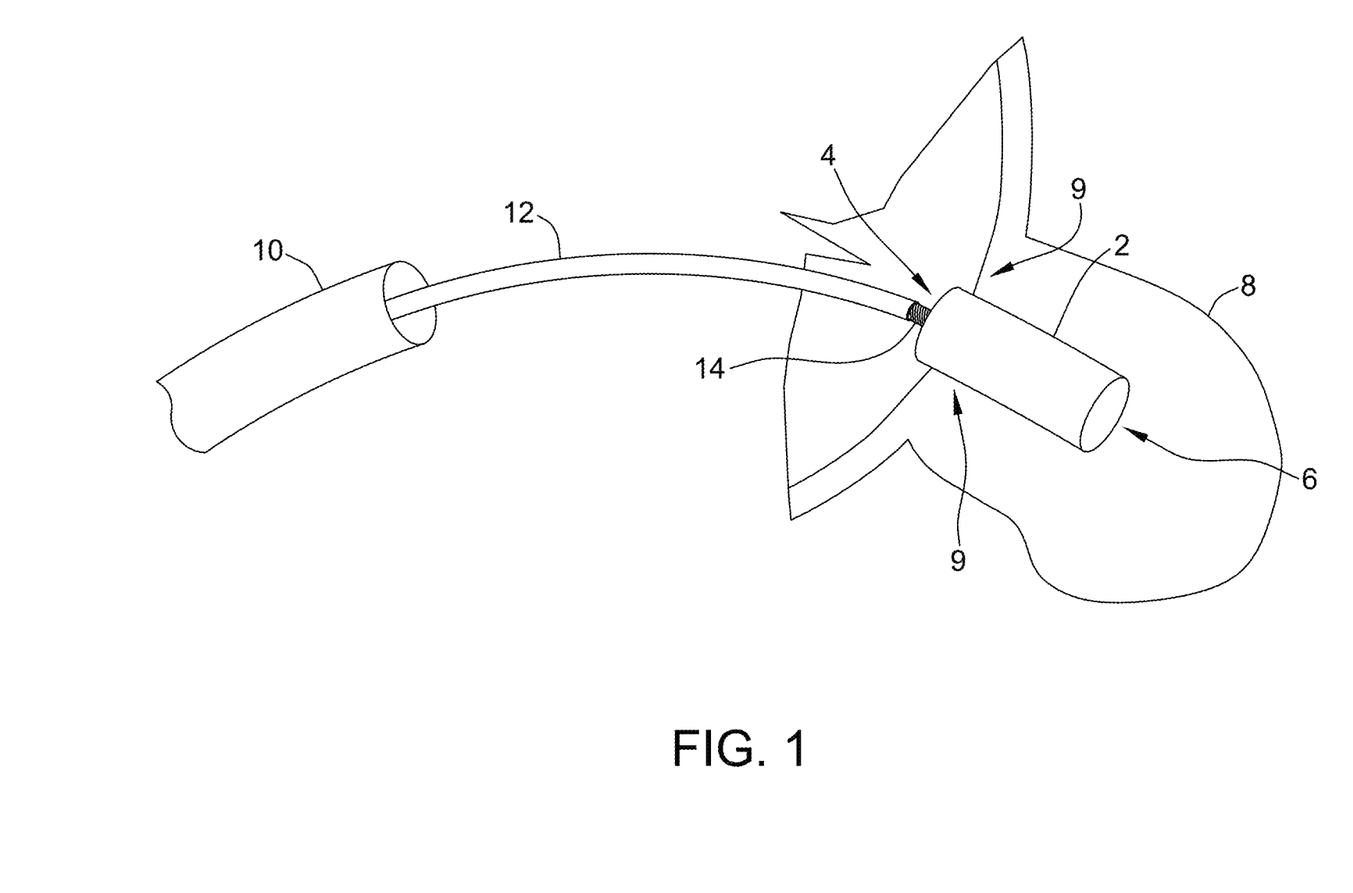
FIG. 1 shows a temperature activated memory shape foam in its first collapsed conformation inside of a left atrial appendage.

Referring now to FIG. 1, there is shown a temperature activated memory shape foam 2 having a proximal end 4 and a distal end 6. Temperature activated memory shape foam 2 is shown its first conformation (collapsed) in FIG. 1, which is the conformation used to introduce temperature activated memory shape foam 2 into the human body (not shown in FIG. 1) and ultimately into left atrial appendage 8. As noted above, temperature activated memory shape foam 2 may optionally include a containment sheath (not shown in FIG. 1) as is known in the art that is pulled back to release temperature activated memory shape foam 2 for expansion inside of the left atrial appendage. As shown in FIG. 1, temperature activated memory shape foam 2 has a generally cylindrical shape in its first conformation (collapsed), although other shapes in the first conformation (collapsed) are within the scope of the present disclosure. Temperature activated memory shape foam 2 is introduced into left atrial appendage 8 through opening 9 using delivery catheter 10 including delivery wire 12. Delivery wire 12 is releasably attached to proximal end 4 of temperature activated memory shape foam 2 using external threads 14, which are connected to an attachment means (shown in one embodiment as element 18 in FIG. 4) on proximal end 4 of temperature activated memory shape foam 2. Once temperature activated memory shape foam 2 is positioned in left atrial appendage 8, delivery wire 12 may be released or disconnected from temperature activated memory shape foam 2 by unscrewing external threads 14 from the attachment means of temperature activated memory shape foam 2 as is known in the art. Additional or alternative embodiments for the attachment means are within the present disclosure as described herein. Alternatively, as described below, delivery wire 12 may remain attached until temperature activated memory shape foam 2 achieves its second expanded conformation.

Figure 2:
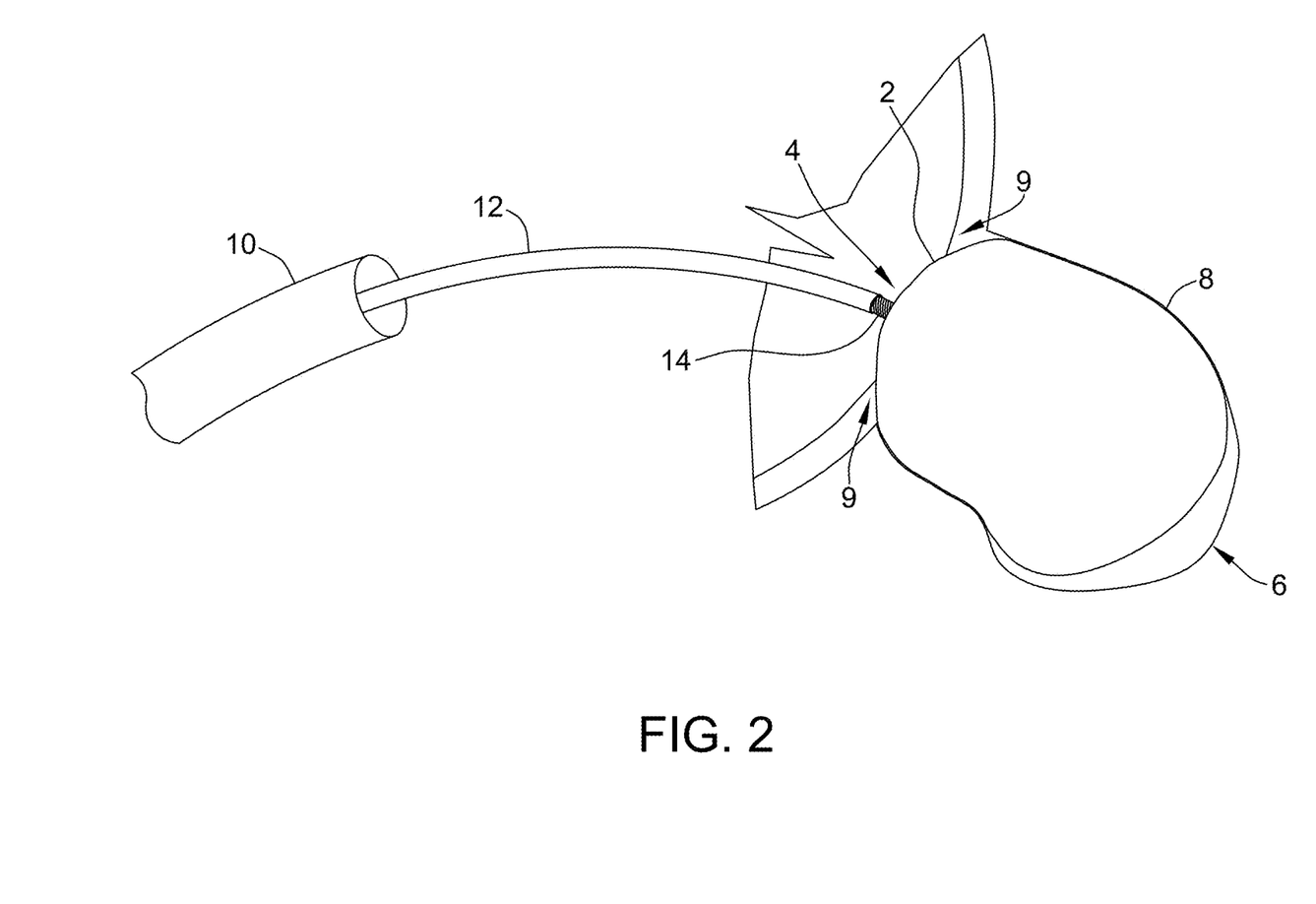
FIG. 2 shows the temperature activated memory shape foam of FIG. 1 in its second expanded conformation inside of a left atrial appendage.
Figure 3:
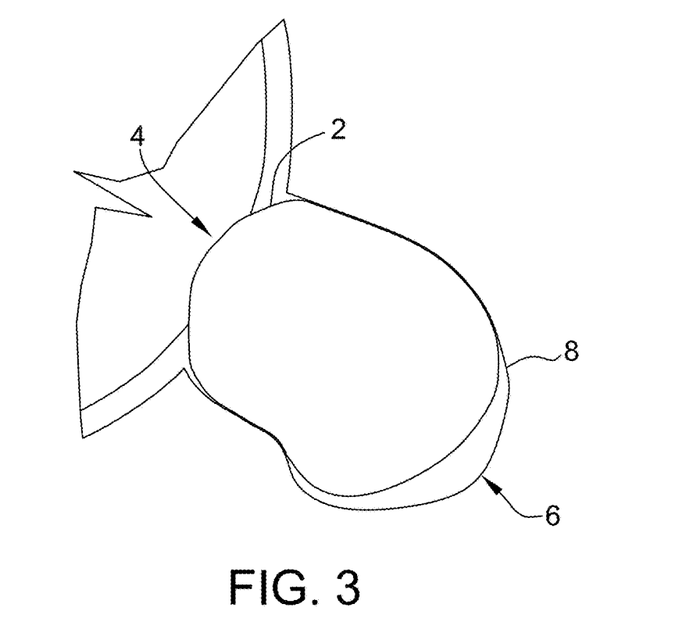
FIG. 3 shows the temperature activated memory shape foam of FIG. 2 released from its delivery wire and positioned inside of a left atrial appendage.

Referring now to FIG. 2, there is shown temperature activated memory shape foam 2 having proximal end 4 and distal end 6 with temperature activated memory shape foam 2 being shown in its second conformation (expanded) inside of left atrial appendage 8. As shown in FIG. 2, temperature activated memory shape foam 2 in its second conformation (expanded) is shaped and configured to conform to the interior of the left atrial appendage, and while still in a generally cylindrical shape, conforms to the general surface shape of the left atrial appendage. This expanded configuration provides an occlusive benefit inside of left atrial appendage 8 as described herein. Once temperature activated memory shape foam 2 has achieved its expanded configuration as illustrated in FIG. 2, delivery wire 12 may be disengaged from the attachment means (not shown in FIG. 2) on proximal end 4 of temperature activated memory shape foam 2 and removed leaving temperature activated memory shape foam 2 in its second conformation (expanded) inside of left atrial appendage 8 as illustrated in FIG. 3.

The temperature activated memory shape foam may be comprised of any suitable material, such as a suitable polymeric material, that is capable of: (1) transitioning from a first collapsed conformation to a second expanded conformation upon being subjected to a specific temperature or temperature range, referred to as a transition temperature; and (2) providing a suitable density in the second conformation for use inside of the left atrial appendage to provide an occlusive benefit while being acutely recapturable and without negatively impacting surrounding anatomy. Suitable transition temperatures may be, for example, from about 37° C. to about 50° C., including from about 37° C. to about 40° C., which allows the temperature activated memory shape foam medical device to assume a first collapsed conformation prior to and during delivery through a delivery catheter or other delivery device, and a second expanded conformation for occlusion after delivery and release within the left atrial appendage. A suitable density of the temperature activated memory shape device in the second (expanded) conformation is a density that allows the second conformation to be pliable and compliant and substantially conform to the left atrial appendage anatomy to create a seal to protect against the formation and escape of blood clots while having sufficient radial force to seal the left atrial appendage but not damage or impact surrounding anatomy. In many embodiments, the density of the temperature activated memory shape foam in the second conformation will be from about 10 $kg/m^3$ to about 1000 $kg/m^3$, including from about 10 $kg/m^3$ to about 500 $kg/m^3$, including from about 10 $kg/m^3$ to about 200 $kg/m^3$, including from about 20 $kg/m^3$ to about 100 $kg/m^3$.

Generally, the material for constructing the temperature activated memory shape foam medical device is a polymeric material that is both biocompatible and substantially biostable. In some embodiments, biocompatibility will include meeting or surpassing the requirements of established standards for implant materials defined in ISO 10993 and USP Class VI. Substantially biostable materials include those materials that do not resorb over the intended lifetime of the medical device (such as five years, or ten years, or longer), as well as those materials that resorb slowly such that void volume is replaced by a stable tissue-like material over a period of a few months to a year.

In some embodiments, the temperature activated memory shape foam medical device may be constructed from a natural and/or synthetic material. Suitable natural materials may include, for example, extracellular matrix (ECM) biopolymers such as collagen, fibronectin, hyaluronic acid and elastin, non-ECM biomaterials such as cross-linked albumin, fibrin, and inorganic bioceramics such as hydroxyapatite and tricalcium phosphate. Suitable synthetic materials may include, for example, biostable polymers such as saturated and unsaturated polyolefins including polyethylene, polyacrylics, polyacrylates, polymethacrylates, polyamides, polyimides, polyurethanes, polyureas, polyvinyl aromatics such as polystyrene, polyisobutylene copolymers and isobutylene-styrene block copolymers such as styrene-isobutylene-styrene tert-block copolymers (SIBS), polyvinylpyrolidone, polyvinyl alcohols, copolymers of vinyl monomers such as ethylene vinyl acetate (EVA), polyvinyl ethers, polyesters including polyethylene terephthalate, polyacrylamides, polyethers such as polyethylene glycol, polytetrahydrofuran and polyether sulfone, polycarbonates, silicones such as siloxane polymers, and fluoropolymers such as polyvinylidene fluoride, and mixtures and copolymers of the above.

In other embodiments, the temperature activated memory shape foam medical device may be constructed from a bioresorbable material such that resorption results in the formation of a biostable tissue matrix. Synthetic bioresorbable polymers may, for example, be selected from the following: (a) polyester homopolymers and copolymers such as polyglycolide (PGA; polyglycolic acid), polylactide (PLA; polylactic acid) including poly-L-lactide, poly-D-lactide and poly-D,L-lactide, poly(beta-hydroxybutyrate), polygluconate including poly-D-gluconate, poly-L-gluconate, poly-D,L-gluconate, poly(epsilon-caprolactone), poly (delta-valerolactone), poly(p-dioxanone), poly(lactide-co-glycolide) (PLGA), poly(lactide-codelta-valerolactone), poly(lactide-co-epsilon-caprolactone), poly(lactide-co-beta-malic acid), poly(beta-hydroxybutyrate-co-beta hydroxyvalerate), poly[1,3bis(p-carboxyphenoxy)propane-co-sebacic acid], and poly(sebacic acid-co-fumaric acid); (b) polycarbonate homopolymers and copolymers such as poly(trimethylene carbonate), poly(lactide-co-trimethylene carbonate) and poly(glycolide-co-trimethylene carbonate); (c) poly (ortho ester homopolymers and copolymers such as those synthesized by copolymerzation of various diketene acetals and diols; (d) polyanhydride homopolymers and copolymers such as poly(adipic anhydride), poly(suberic anhydride), poly (sebacic anhydride), poly(dodecanedioic anhydride), poly(maleic anhydride), poly[1,3-bis-(p-carboxyphenoxy) methane anhydride], and poly[alpha,omega-bis(p-carboxyphenoxy)alkane anhydride] such as poly[1,3-bis(p-carboxyphenoxy)propane anhydride] and poly[1,3-bis(p-carboxyphenoxy)hexane anhydride]; (e) polyphosphazenes such as aminated and alkoxy substituted polyphosphazenes; and (f) amino-acid-based polymers including tyrosine-based polymers such as tyrosine-based polyacrylates (e.g., copolymers of a diphenol and a diacid linked by ester bonds, with diphenols selected, for example, from ethyl, butyl, hexyl, octyl, and benzyl esters of desaminotyrosyl-tyrosine and diacids selected, for example, from succinic, glutaric, adipic, suberic, and sebacic acid), tyrosine-based polycarbonates (e.g., copolymers formed by the condensation polymerization of phosgene and a diphenol selected, for example, from ethyl, butyl, hexyl, octyl, and benzyl esters of desaminotyrosyl-tyrosine, tyrosine-based iminocarbonates, and tyrosine-, leucine- and lysine-based polyester-amides; specific examples of tyrosine-based polymers further include polymers that are comprised of a combination of desaminotyrosyl tyrosine hexyl ester, desaminotyrosyl tyrosine, and various di-acids, for example, succinic acid and adipic acid. Particularly desirable materials include cross-linked polycarbonates and crosslinked polyethylene glycols.

As noted above, the temperature activated memory shape foam has a thermal transition point (transition temperature) below which residual stress is maintained without a loading constraint. The thermal activation (which causes the shape memory) may be achieved with the desired material going through a semi-crystalline melt point or glass transition temperature between the first conformation (collapsed) and the second conformation (expanded). Several suitable thermal activation processes are known in the art and useful herein. In one suitable embodiment, the temperature activated memory shape foam may be formed for use as a medical device by first shaping a temperature activated memory foam formed from a suitable material into its final expanded (second) conformation; that is, the conformation that the temperature activated memory shape foam will achieve once inserted into the left atrial appendage to provide the desired occlusive benefit. In this final expanded (second) conformation, the temperature activated memory foam will generally have a diameter that will range from about 10 millimeters to about 35 millimeters and a length that will range from about 2 centimeters to about 5 centimeters, although other diameters and lengths are within the scope of the present disclosure. Once this has been done, the formed conformation is heated above the transition temperature of the material; that is, the temperature at which a desired conformational change will occur. As noted above, suitable transition temperatures may be from about 37° C. to about 50° C. Once the desired transition temperature has been achieved, the temperature activated memory shape foam is held at a constant temperature and is re-shaped into a collapsed (first) conformation sized and configured for insertion through a delivery catheter or the like. This re-shaping is suitably done in a properly sized molding element and may be any suitable shape, although in many embodiments a generally cylindrical shape is desirable. In this collapsed (first) conformation, the temperature activated memory foam will generally have a diameter of less than 4.7 millimeters and a length that will range from about 2 centimeters to about 5 centimeters, although other diameters and lengths are within the scope of the present disclosure. After insertion into the molding element, the temperature is reduced to a temperature below the transition temperature to set the new shape; for example, the temperature may be reduced to room temperature to set the new shape (first collapsed conformation). Once this has been completed, the temperature activated memory shape foam will remain in its first (collapsed) conformation until it is subjected to a temperature at or above the transition temperature, at which time it will expand into its second (expanded or remembered) conformation.

Generally, the second expanded conformation is achieved in the left atrial appendage after the temperature activated memory shape foam has been introduced therein. Because the human body is generally at a temperature of 37° C. or more, the natural body temperature within the left atrial appendage will cause the change from the first conformation to the second conformation within the left atrial appendage when the transition temperature is set at less than or equal to 37° C. In some embodiments of the present disclosure, a solution heated to a temperature above the transition temperature, such as a heated saline solution, may be injected into the left atrial appendage during or after insertion of the temperature activated memory shape foam to cause to foam to expand, or expand more rapidly as compared to the expansion that would occur at the body temperature or another elevated temperature.

Figure 4:
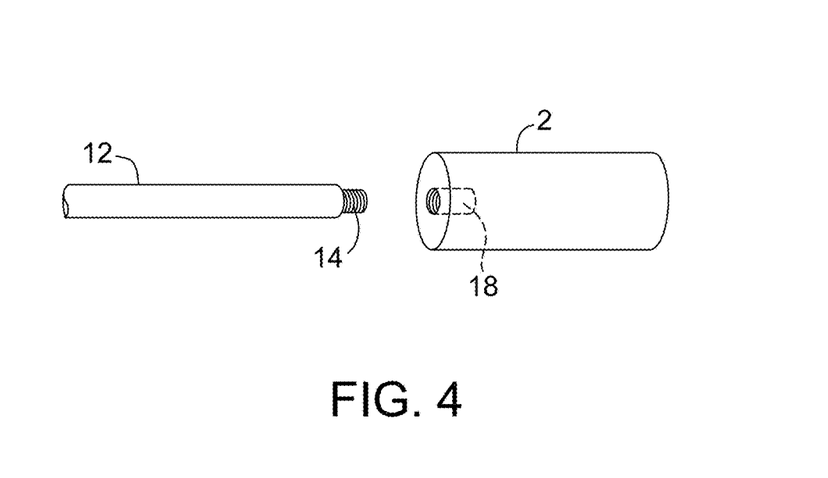
FIG. 4 shows the temperature activated memory shape foam of FIG. 1 including an attachment means.

As noted above in reference to FIGS. 1 and 2, temperature activated memory shape foam 2 includes an attachment means (not shown in FIGS. 1 and 2) to allow temperature activated memory shape foam 2 to be attached to delivery wire 12 (or another suitable delivery device) using external threads 14 (or any other suitable attachment means) for delivery into left atrial appendage 8, and recaptured and removed or repositioned, if necessary. Any attachment means known in the art may be suitable for use with temperature activated memory shape foam 2 and delivery wire 12, so long as delivery wire 12 can engage temperature activated memory shape foam 2, properly position it within left atrial appendage 8, and release it and recapture it, if necessary. In one exemplary desirable embodiment, conventional male and female screw connections, such as that illustrated in FIG. 4 are utilized. FIG. 4 shows temperature activated memory shape foam 2 (in its collapsed conformation) including internally threaded center end screw 18 and delivery wire 12 including external threads 14. Temperature activated memory shape foam 2 may be easily connected to, and disconnected from, delivery wire 12 using internally threaded center end screw 18 in combination with external threads 14. Internally threaded center end screw 18 may generally be constructed of any suitable metal, including for example, stainless steel and may, in some embodiments, include a radiopaque marker to increase visibility under fluoroscopy.

As will be recognized by one skilled in the art based on the disclosure herein, the exact attachment mechanisms used to connect delivery wire 12 and temperature activated memory shape foam 2 are not critical and many suitable alternatives exist. In one alternative embodiment, a keyed feature and key hole as is known in the art could be used in place of internally threaded center end screw 18 and external threads 14 as shown in FIG. 4. In a further alternative embodiment, temperature activated memory shape foam 2 is introduced and released into left atrial appendage 8 (as shown in FIG. 3) using a sheath and pusher wherein the radial force of temperature activated memory shape foam 2 against the sheath would hold it in place at the end of the sheath such that it could be pushed out and into left atrial appendage 8 with a suitable push cable. In another alternative embodiment a mechanical release mechanism could be used to place and release temperature activated memory shape foam 2 wherein a locking mechanism on a delivery wire fastens to a feature on temperature activated memory shape foam 2 such that it may be released after positioning by pushing the mechanism forward, backward, or rotating. In a further alternative embodiment, delivery wire 12 could be equipped with conventional detents to hold and release temperature activated memory shape foam 2. Other suitable alternative embodiments include using sutures, bioadhesives, magnets, break mechanisms, and/or piezoelectric mechanisms as are known in the art.

Figure 5:
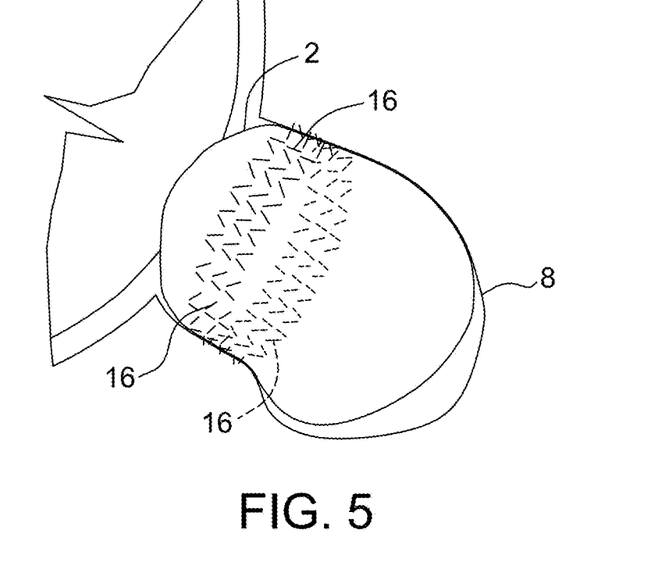
FIG. 5 shows the temperature activated memory shape foam of FIG. 3 further including an anchoring mechanism.

Referring now to FIG. 5, in some embodiments of the present disclosure, it may be desirable to fit temperature activated memory shape foam 2 with anchoring mechanism 16 to assist in holding temperature activated memory shape foam 2 inside of left atrial appendage 8 in the desired location once properly positioned. Anchoring mechanism 16 may be any anchoring mechanism known in the art and may include, for example, spikes and/or hooks, which may or may not include barbs on some or all of the spikes and/or hooks. In a desirable embodiment, anchoring mechanism 16 comprises hooks that are configured to penetrate the wall of left atrial appendage 8, but are also configured so as not to extend completely through the wall of left atrial appendage 8 such that any potential for the incidence of effusion is reduced or eliminated. Only a portion or all of temperature activated memory shape foam 2 may be covered with anchoring mechanism 16.

Figure 6:
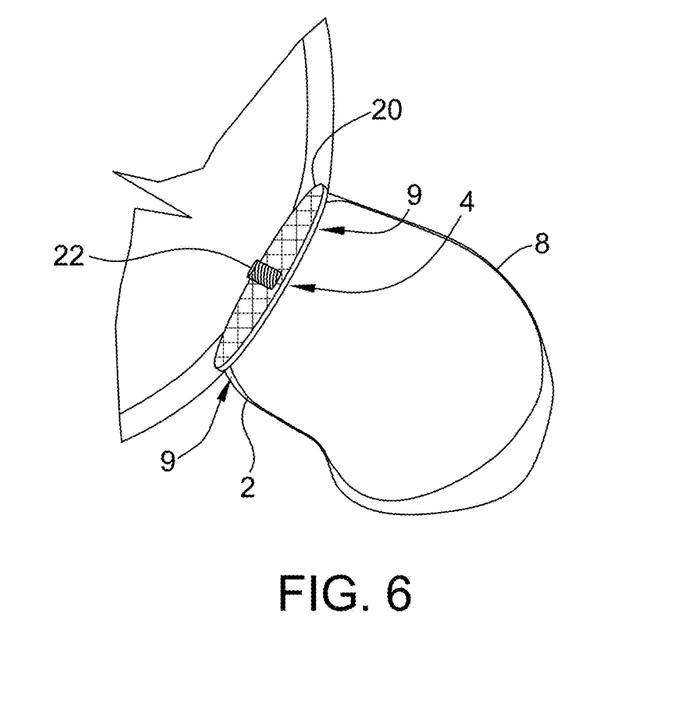
FIG. 6 shows the temperature activated memory shape foam of FIG. 3 further including a disc-shaped member to enhance occlusion.

In some embodiments of the present disclosure, it may be desirable to provide an additional barrier at the opening of the left atrial appendage to further seal the left atrial appendage and reduce any potential for the formation and escape of blood clots therefrom. In one alternative embodiment, a disc-shaped member may be utilized in combination with the temperature activated memory shape foam described above to provide additional benefits to the resulting medical device that includes a temperature activated memory shape foam coupled to a disc-shaped member. Referring now to FIG. 6, there is shown a disc-shaped member 20 having attachment means 22 for connecting to a delivery device (not shown in FIG. 6 but similar to delivery wire 12 of FIG. 1). Disc-shaped member 20 is attached to proximal end 4 temperature activated memory shape foam 2 with a suitable connecting means (not shown in FIG. 6), such that temperature activated memory shape foam 2 may be located inside left atrial appendage 8. Disc-shaped member 20 is sized and configured to substantially or fully cover opening 9 in left atrial appendage 8. Disc-shaped member 20 acts to stabilize temperature activated memory shape foam 2 within left atrial appendage 8, while additionally closing off and further sealing opening 9 of left atrial appendage 8 to provide further protection against blood clots (not shown in FIG. 6) from forming and escaping from left atrial appendage 8.

Disc-shaped member 20 may be constructed of any suitable material that may be reduced in size for delivery through a delivery catheter or other delivery device as known in the art while possessing sufficient strength in an unconstrained configuration to seal off opening 9 in left atrial appendage 8. In its unconstrained configuration (i.e., after ejection from a delivery catheter), disc-shaped member 20 is sized and configured to cover and seal opening 9 in left atrial appendage 8, as noted above. One class of materials that is desirable for constructing disc-shaped member 20 includes memory-shape alloys. Such alloys tend to have a temperature induced phase change that will cause the material to have a remembered configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in constructing the disc-shaped portion is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a medical device return to an expanded configuration for deployment inside of the body following passage in a distorted or collapsed form through a delivery catheter. Nitinol is a particularly desirable alloy for forming the disc-shaped portion described above. In some embodiments of the present disclosure, disc-shaped member 20 may include a therapeutic membrane as known in the art to further occlusion.

Disc-shaped member 20 may be connected or attached to temperature activated memory shape foam 2 using any suitable connecting means that allows for a secure connection prior to, during, and after delivery of the combination to left atrial appendage 8. In one embodiment, disc-shaped member 20 may be connected to proximal end 4 of temperature activated memory shape foam 2 using one or more sutures, one or more bioadhesives, or a combination of one or more sutures and one or more bioadhesives. Alternatively, the connecting means may include one or more other connecting means known in the art such as center end screws and threads, and the like.

As noted above and shown in FIG. 6, disc-shaped member 20 includes attachment means 22 for connecting disc-shaped member 20, and hence temperature activated memory shape foam 2 to a delivery device (not shown in FIG. 6, but similar to delivery wire 12 shown in FIG. 1). Attachment means 22 may be any suitable attachment means for connecting disc-shaped member 20 to a delivery device, and is desirably a center end screw as described above, although all embodiments described above for connecting a temperature activated memory shape foam to a delivery device could similarly be used to connect disc-shaped member 20 to a delivery device.

In some other embodiments of the present disclosure, it may be advantageous to encapsulate the temperature activated memory shape foam in its first collapsed conformation for delivery into the left atrial appendage with a mesh or similar material, such as a braided nitinol, or other suitable framework that expands with the temperature activated memory shape foam upon the temperature activated memory shape foam assuming its expanded conformation at and above the transition temperature described above. Alternatively, in other embodiments of the present disclosure, it may be desirable to coat the mesh with the temperature activated memory shape foam such that the temperature activated memory shape foam is located on the exterior of the mesh (i.e., the mesh is interior of the temperature activated memory shape foam) and is free to expand due to the properties of the underlying mesh. Upon expansion, the mesh structure attains a more rigid and closed form as the temperature activated memory shape foam is activated.

Figure 7:
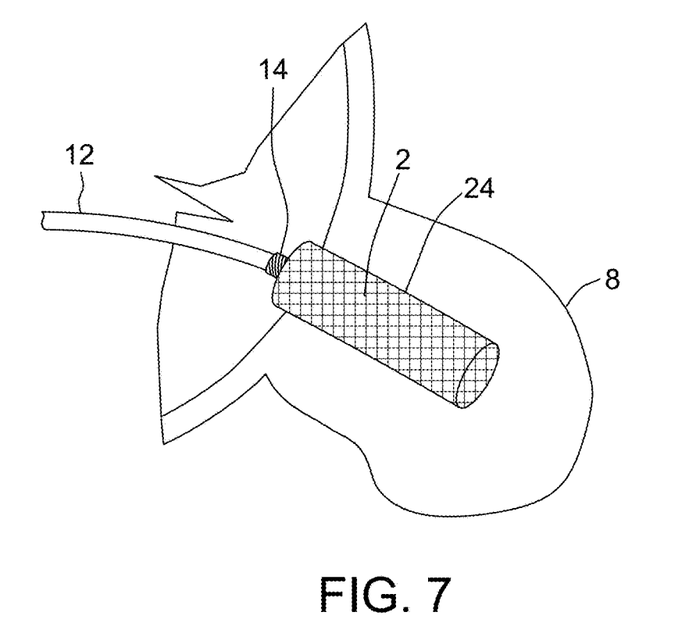
FIG. 7 shows the temperature activated memory shape foam of FIG. 1 further including a mesh material encapsulating the temperature activated memory shape foam.
Figure 8:
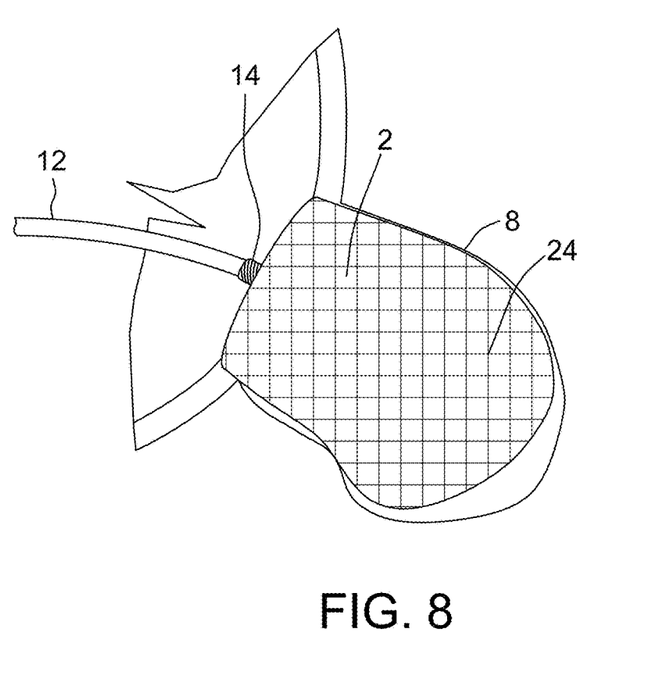
FIG. 8 shows the temperature activated memory shape foam of FIG. 2 further including a mesh material encapsulating the temperature activated memory shape foam.

Referring now to FIG. 7, there is shown temperature activated memory shape foam 2 in its collapsed conformation surrounded by mesh 24. Temperature activated memory shape foam 2, including mesh 24, may be inserted into left atrial appendage 8 using delivery wire 12 including external threads 14, which are connected to an attachment means (not shown in FIG. 7 but similar to that of internally threaded center end screw 18 in FIG. 4) on temperature activated memory shape foam 2. FIG. 8 shows temperature activated memory shape foam 2 in its expanded configuration with mesh 24 also expanded to continuously encapsulate temperature activated memory shape foam 2 within left atrial appendage 8 and provide the benefits discussed below.

Any type of shape memory alloy or other suitable material may be used to construct mesh 24, with nitinol as described above being a desirable braiding material due to its superior memory characteristics and elastic properties. Mesh 24 provides stability during expansion of the device, as well as additional shape memory features, radial strength, anchoring assistance, and structure to the resulting device, while still allowing temperature activated memory shape foam 2 to provide an occlusive benefit as detailed herein. Additionally, mesh 24 may also provide a recapture benefit by assisting in the collapsing of temperature activated memory shape foam 2 should recapture/reposition/removal be desired, as described below.

The combination of mesh 24 encapsulating temperature activated memory shape foam 2 may be constructed by any suitable means. In one embodiment, a memory shape alloy such as a nitinol mesh is used as mesh 24 and is first set in a suitable mold at an elevated temperature as is known in the art to provide the nitinol mesh with its memory properties such that it may expand and contract as directed by temperature activated memory shape foam 2. After the nitinol mesh is formed, a suitable temperature activated memory shape foam in its collapsed conformation (that is, temperature activated memory shape foam 2 is at a temperature below its transition temperature) is introduced into the nitinol mesh. Temperature activated memory shape foam 2 will generally include an attachment means (for example, similar to internally threaded center end screw 18 in FIG. 4) for accepting a delivery wire or other suitable delivery device to allow the combination of the nitinol mesh/temperature activated memory shape foam to be guided into left atrial appendage 8. Other methods of introducing an attachment means onto the combination of the nitinol mesh/temperature activated memory shape foam are also with the scope of the present disclosure. After temperature activated memory shape foam 2 has been introduced into nitinol mesh 24, the combination may be attached to a delivery wire and introduced into left atrial appendage 8 for use.

Figure 9:
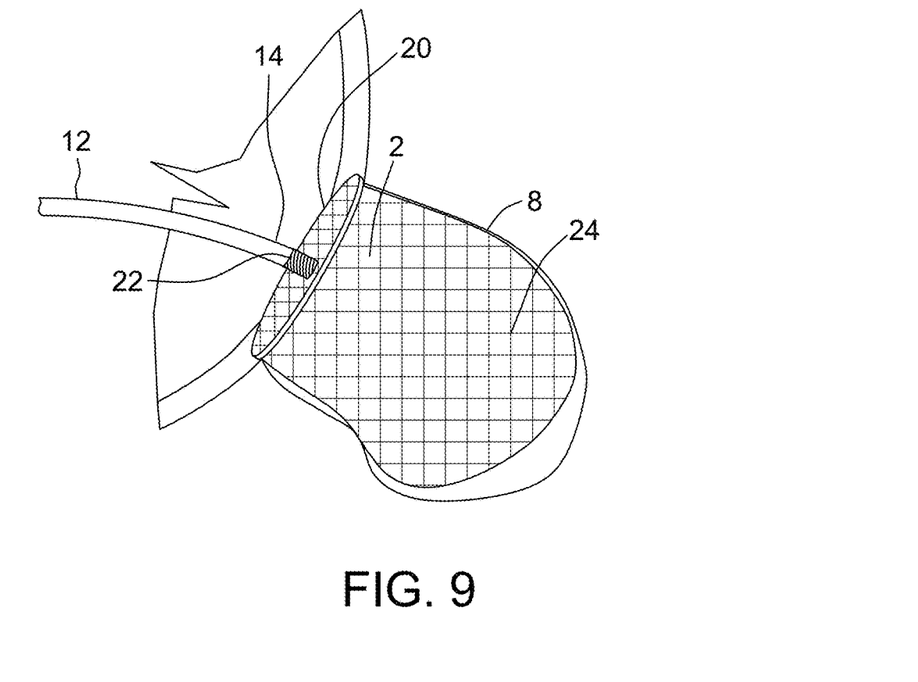
FIG. 9 shows the temperature activated memory shape foam of FIG. 8 further including a disc-shaped member to enhance occlusion.

In another embodiment of the present disclosure and now referring to FIG. 9, temperature activated memory shape foam 2 and mesh 24 as shown in FIGS. 7 and 8 may be used in combination with disc-shaped member 20 as described above in relation to FIG. 6 to provide additional benefits as noted herein to the resulting medical device.

In many embodiments of the present disclosure the medical devices including the temperature activated memory shape foam are advantageously recapturable within a delivery device such that in the event that it is desired to reposition or completely remove the medical device once it has been deployed in the left atrial appendage and expanded into its second conformation, it can be safely recaptured. The medical devices described herein and including a temperature activated memory shape foam are highly compliant and compressible, which aids in their ability to be acutely recapturable. A number of different methodologies may be used to recapture the temperature activated memory shape foam. In one embodiment, the medical device in its expanded conformation may be recaptured by introducing heat onto the medical device to increase compliance and make the medical device easier to compress and recapture. In many embodiments, the any recapture and repositioning/redeployment will be completed prior to disconnecting the delivery wire from the attachment means. In those embodiments where the delivery wire had been disconnected from the attachments means and recapture is desired, the delivery wire may be reconnected to the attachment means, or a snare or other similar device may be used to assist in the recapture of the medical device. Heat may be applied to the medical device to increase compliance in any number of ways including, for example, flushing the medical device with a warm liquid utilizing a multi-lumen sheath as is known in the art. The multi-lumen sheath may have a separate flushing lumen to deliver a warmed fluid, such as a warmed saline solution, to the medical device. Additionally, or alternatively, electric coils or another heating mechanism may be placed at the end of the delivery device or delivery sheath such that upon the application of electricity, the electric coils become warm and heat the medical device to increase compliance such that it may be more easily recaptured into the delivery device.

A number of other methods for recapturing the temperature activated memory shape foam may also be used in accordance with the present disclosure including, for example, split sheaths with one or multiple slits at the end to assist in guiding the device therein and sheaths including an expanding funnel member for guiding the device and being constructed of a shape memory alloy such as nitinol. Other methods may include the use of a helical wire or ribbon that spirals around the device such that if recapture is desirable the wire or ribbon may be tightened to compress the device for recapture. Other methods for recapture are also within the scope of the present disclosure.

In another embodiment of the present disclosure, a medical device for occluding a left atrial appendage includes a flowable thermoset that may be introduced through a single or multi-lumen delivery catheter and into the left atrial appendage in a flowable liquid and/or gel form. The flowable thermoset may be introduced into the left atrial appendage without the use of a containment device, or it may be introduced directly into a balloon or similar containment device located within the left atrial appendage such that the filled balloon or similar containment device remains in place in the left atrial appendage after filling. The liquid and/or gel assumes the conformation of the left atrial appendage and upon solidification provides an occlusive benefit inside of the left atrial appendage as discussed herein. The flowable thermoset may be constructed from a single liquid or gel, or may be constructed from two, three or more liquids or gels as described herein that are mixed together prior to, during, or after introduction into the left atrial appendage through a delivery catheter or other suitable delivery means. The flowable thermoset forms a type of solid, pliable polymer plug that fills all or a portion of the left atrial appendage, while conforming to the anatomy of the left atrial appendage to provide a tight seal that is substantially non-damaging to the surrounding anatomy. The flowable thermoset-based medical device further optionally includes a flow or distribution member attached to the delivery catheter (or integral with the delivery catheter) that extends into the left atrial appendage to deliver the flowable thermoset therein. In many embodiments, small-sized delivery catheters may be used in combination with the flowable thermoset as the liquid or gel does not require a large channel to pass into the left atrial appendage. In many embodiments, a 6 French or smaller delivery catheter or similar device may be utilized.

The flowable thermoset may be delivered to the left atrial appendage using any means known in the art for delivering a liquid and/or gel to a desired hole, channel, or opening in the body. In many embodiments of the present disclosure, the flowable thermoset is delivered into the left atrial appendage using a single delivery catheter that may or may not include a means for directing or blocking the flow of the flowable thermoset within, or near, the left atrial appendage. The delivery catheter may include one or more actuating plungers or syringes to facilitate delivery of the flowable thermoset. In those embodiments where the flowable thermoset comprises two or more components, the components may be mixed at or near the proximal end of the delivery catheter. In other embodiments, the delivery catheter may include multiple lumens to carry the flowable thermoset components to the distal end of the catheter for mixing. The delivery catheter may also include one or more mixing elements along its length.

In some embodiments described herein, the distal end of the delivery catheter may include means for directing or blocking the flow of the flowable thermoset. In one specific embodiment, the blocking means may include a self-expanding disc member that may be located at the proximal end of the delivery catheter such that it blocks the opening into the left atrial appendage and seals it such that flowable thermoset cannot leak therefrom. This disc member may be permanently implanted or may be recoverable. Another suitable blocking mechanism may be an expandable balloon, as is known in the art.

Figure 10:
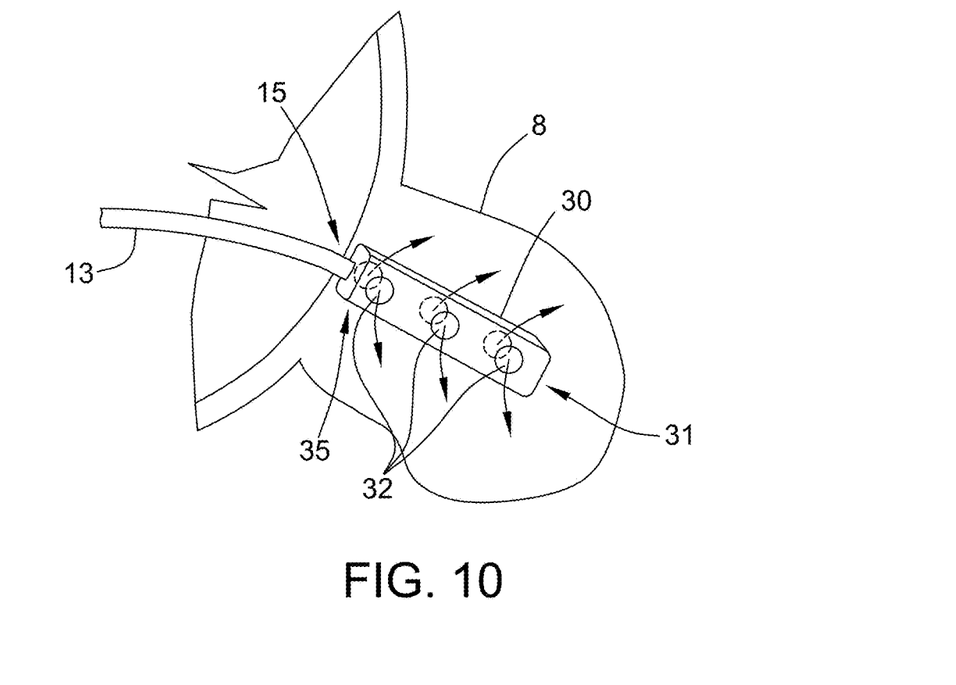
FIG. 10 shows a flow member for receiving a liquid or gel flowable thermoset for introduction into a left atrial appendage.

Referring now to FIG. 10, there is shown optional flow or distribution member 30 extending into left atrial appendage 8 and further including openings 32 therein. Flow or distribution member 30 is shown in FIG. 10 as a separate piece from delivery catheter 13, but it should be recognized that it is within the scope of the present disclosure for flow or distribution member 30 to be integral with delivery catheter 13 such that it is a single component. Flow or distribution member 30 has a distal end 31 and a proximal end 35 with proximal end 35 being attached to, or integral with, distal end 15 of delivery catheter 13. Flow or distribution member 30 is attached to delivery catheter 13 such that a flowable thermoset (element 36 shown in FIG. 12) can be received from delivery catheter 13 into flow or distribution member 30 and pass through openings 32 and into left atrial appendage 8. Once the flowable thermoset (not shown in FIG. 10) has been introduced into left atrial appendage 8, it is allowed to solidify therein such that it can provide an occlusive benefit.

Figure 11:
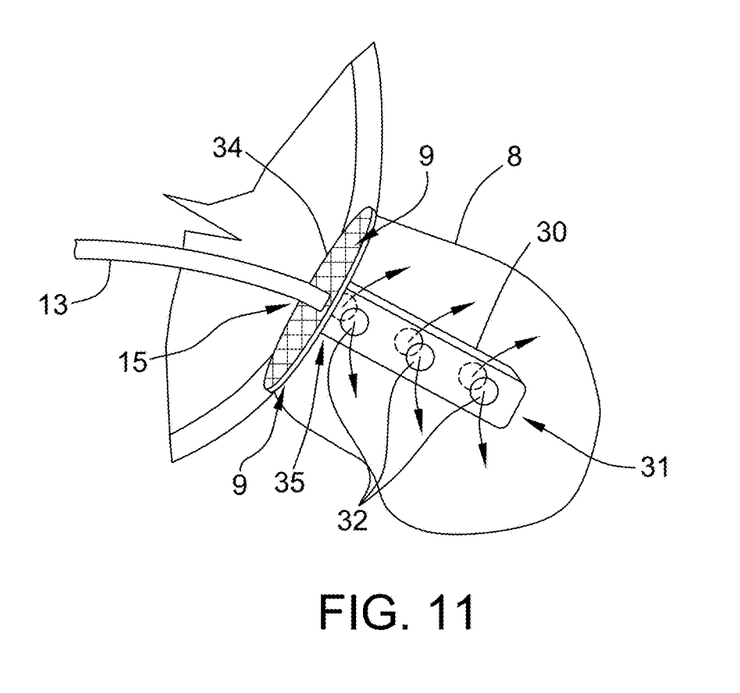
FIG. 11 shows the flow member of FIG. 10 further including a disc-shaped member for sealing a left atrial appendage.

As shown in FIG. 11, in many embodiments, a disc member 34, or other suitable blocking member, may be used in combination with delivery catheter 13 to form part of the medical device. Disc member 34 is attached to distal end 15 of delivery catheter 13 and to proximal end 35 of flow or distribution member 30 and provides a barrier at opening 9 of left atrial appendage 8 to hold the injected flowable thermoset (element 36 shown in FIG. 12) in place until solidification such that the flowable thermoset does not escape from left atrial appendage 8. Disc member 34 may be comprised of any suitable material, such as a memory shape alloy including nitinol. Disc member 34 as shown in FIG. 11 may be constructed and attached to flow or distribution member 30 and delivery catheter 13 in any suitable manner including those described hereinabove.

Figure 12:
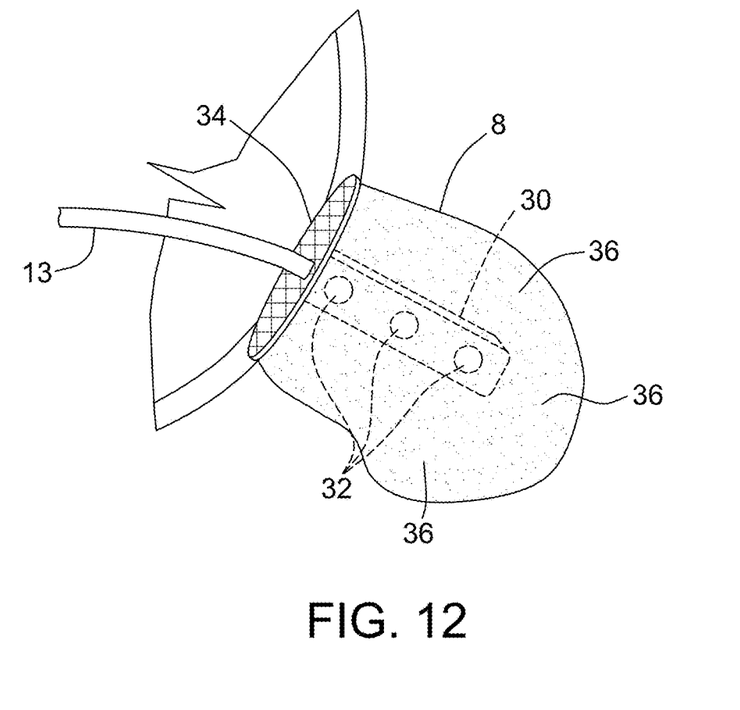
FIG. 12 shows the flow member and disc-shaped member of FIG. 11 further including a flowable thermoset inside of a left atrial appendage.

Referring now to FIG. 12, there is shown left atrial appendage 8 including flowable thermoset 36 therein. Flowable thermoset 36 conforms to the anatomy of left atrial appendage to form a seal to provide an occlusive benefit within left atrial appendage 8. Also shown is flow or distribution member 30 including openings 32, disc member 34, and delivery catheter 13. In those embodiments where disc member 34 is utilized to provide a barrier to prevent flowable thermoset 36 from escaping left atrial appendage 8 prior to solidification, disc member 34 may be removed from left atrial appendage 8 after solidification, or may remain in place after solidification to provide an additional sealing benefit.

In an alternative embodiment, flowable thermoset 36 may be introduced into left atrial appendage 8 through flow or distribution member 30 without the use of disc member 34 such that flow or distribution member 30 is extracted from left atrial appendage 8 before solidification of flowable thermoset 36. In this embodiment, flow or distribution member 30, while connected to delivery catheter 13, may be introduced into left atrial appendage 8 and extracted slowly or telescopically while flowable thermoset 36 is injected into left atrial appendage 8. Once the desired amount of flowable thermoset 36 has been introduced into left atrial appendage 8, flow or distribution member 30 is extracted from left atrial appendage 8 and solidification may occur such that an occlusive benefit is realized.

Flowable thermoset 36 may be constructed of a single component, or may be constructed of multiple components that are mixed together as noted above prior to solidification within left atrial appendage 8. In some embodiments, flowable thermoset 36 may be doped with a radiopaque agent to assist a practitioner in verifying the extent of occlusion of left atrial appendage 8 after introduction of the flowable thermoset therein. The radiopaque agent may be any suitable radiopaque agent including, for example, barium, iodine, or other known contrast agents.

Flowable thermoset 36 may be naturally derived or may be synthetic. Examples of synthetic components include polyethers such as polyethylene glycol, polypropylene glycol, and polytetrahydrofuran, polyamine compositions such as polyvinylpyrrolidones and polyethylene imines, and polyacrylic and methacrylic compounds such as polyacrylic acid. Examples of naturally derived components include proteinaceous compositions such as albumin, collagen, and polylysine, and carbohydrate compositions such as polyhyaluronic acid.

Flowable thermoset 36 may be chemically cross-linked by any known method including, for example, condensation reactions, Michael addition, and free radical addition. Functional groups used for the cross-linking reaction may include, for example, thiols, acrylates, amines, succinimydyls, and aldehydes. In some embodiments, flowable thermoset 36 may expand and solidify as a single component that undergoes a thermal transition or chemical reaction. Examples of a thermal transition include materials that phase separate and solidify when going from room temperature to body temperature, including various polypropylene glycol and acrylamide-based copolymers that undergo LCST thermal transition to a solid phase at temperatures between about 20° C. and about 40° C. Examples of a chemical reaction include polymers that undergo microphase separation upon a pH change such as with various copolymers of acrylic acids.

Flowable thermoset 36 will solidify or cure within left atrial appendage 8 in a desirable time to provide the occlusive benefit. In some embodiments, the cure time will be from about 1 second to about 10 minutes, including from about 5 seconds to about 5 minutes, including from about 5 seconds to about 1 minute. In some desirable embodiments, the cure time will be less than about 30 seconds, including less than about 20 seconds, including less than about 10 seconds. When in its cured or solidified state, the flowable thermoset will have a density of from about 10 kg/m$^3$ to about 200 kg/m$^3$, including from about 20 kg/m$^3$ to about 100 kg/m$^3$.

Although a number embodiments of this disclosure have been described above with a certain degree of particularity, those skilled in the art could make numerous alterations to the disclosed embodiments without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

Example 1

The following Example illustrates a specific embodiment and/or feature of a medical device including a flowable thermoset for occluding a left atrial appendage of the present disclosure. The Example is given solely for the purpose of illustration and is not to be construed as a limitation of the present disclosure, as many variations thereof are possible without departing from the spirit and scope of the disclosure.

Figure 13:
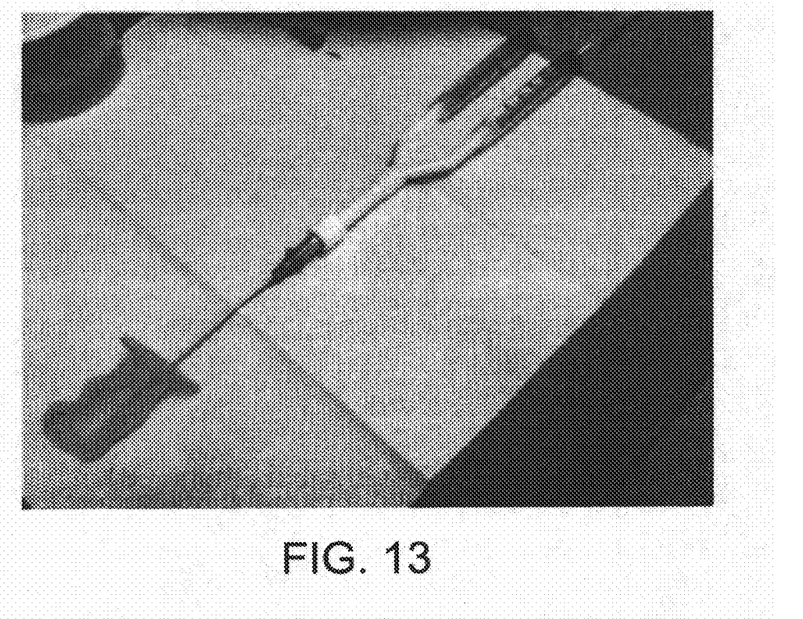
FIG. 13 is a photograph showing a two syringe injection and mixing system introduced into a silicone model of a left atrial appendage of Example 1.

In this Example, a medical device for occluding a left atrial appendage of the present disclosure and including a flowable thermoset was introduced into a silicone model of a left atrial appendage to evaluate the occlusive benefit by analyzing the ability of the flowable thermoset to conform to the size and shape of the silicone model prior to and after solidification. The silicone model had an orifice diameter of about 18 millimeters and a volume of about 7 milliliters. The flowable thermoset was comprised of a two-component system with the first component being a 38 wt. % bovine serum albumin in saline solution and the second component being a 12 wt. % glutaraldehyde in deionized water solution. The total percent solids was about 25 wt. %. The two component system was simultaneously injected into the silicone left atrial appendage model using a two syringe injection and mixing system (Nordson Micromedics SA-3675 with dual 3 cc syringes (St. Paul, Minn.)) such that the components had been mixed together prior to injection into the silicone model. The cure time for the two-component flowable thermoset was less than 10 seconds such that the flowable thermoset solidified nearly instantly upon being injected into silicone model left atrial appendage. FIG. 13 is a photograph showing the two syringe injection and mixing system utilized to inject the components into the silicone model left atrial appendage.

Figure 14:
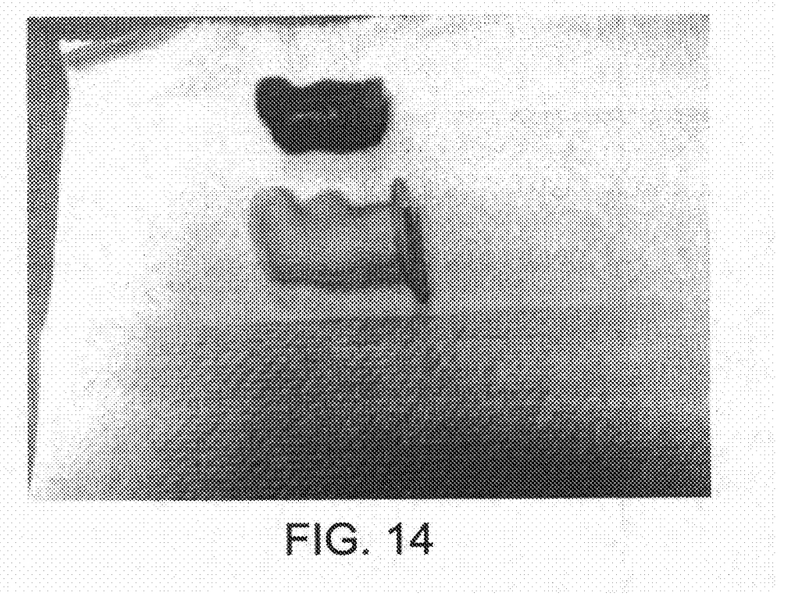
FIG. 14 is a photograph showing a solid flowable thermoset after removal from a silicone model left atrial appendage (top structure) and the silicone model left atrial appendage (bottom structure) of Example 1.

After solidification, the solid flowable thermoset was removed from the silicone model left atrial appendage for evaluation. FIG. 14 is a photograph showing the solid flowable thermoset after removal from the silicone model left atrial appendage (top structure) and the silicone model left atrial appendage (bottom structure). As shown in FIG. 14, the shape of the solid flowable thermoset is nearly identical to the silicone model left atrial appendage indicating that the flowable thermoset conformed to the structure of the silicone model left atrial appendage and would have provided a significant occlusive benefit due to a tight, compliant fit therein.

What is claimed is:

1. A medical device for occluding a left atrial appendage, the medical device comprising:
   a foam structure having a distal end and a proximal end, the foam structure being constructed to transition from a first conformation to a second conformation upon an increase in temperature, wherein the second conformation is configured to occlude the left atrial appendage; and
   a disc member coupled to the proximal end of the foam structure and including an attachment means sized and configured for attachment to a delivery device.

2. The medical device of claim 1, wherein the foam structure is comprised of a material selected from the group consisting of naturally derived materials, synthetic materials, bioresorbable materials, and combinations thereof.

3. The medical device of claim 1, wherein the foam structure in the second conformation has a density from about 10 kg/m$^3$ to about 200 kg/m$^3$.

4. The medical device of claim 1, wherein the foam structure has a transition temperature from about 37° C. to about 50° C.

5. The medical device of claim 1, wherein the first conformation of the foam structure is generally cylindrical.

6. The medical device of claim 1, further comprising:
   at least one fixture component to stabilize the foam structure in the left atrial appendage.

7. The medical device of claim 1, further comprising:
   a mesh surrounding the foam structure, wherein the mesh is sized and configured to transition from a first conformation to a second conformation.

8. The medical device of claim 1, further comprising:
   a mesh interior the foam structure, wherein the mesh is sized and configured to transition from a first conformation to a second conformation.

9. The medical device of claim 8, wherein the mesh comprises nitinol.

* * * * *